(12) United States Patent  
Clark et al.

(10) Patent No.: US 6,774,241 B2
(45) Date of Patent: Aug. 10, 2004

(54) 1-SULFONYL-4-AMINOALKOXY INDOLE DERIVATIVES AND USES THEREOF

(75) Inventors: Robin Douglas Clark, Lawai, HI (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 10/454,050

(22) Filed: Jun. 4, 2003

(65) Prior Publication Data

US 2003/0229069 A1 Dec. 11, 2003

Related U.S. Application Data

(60) Provisional application No. 60/386,049, filed on Jun. 5, 2002.

(51) Int. Cl.$^7$ .................... C07D 209/04; C07D 413/02; C07D 401/02
(52) U.S. Cl. ................... 548/491; 544/144; 546/207; 546/178; 548/465
(58) Field of Search ................ 548/491, 465; 546/178, 201; 544/144; 514/415, 414, 315, 235.2

(56) References Cited

U.S. PATENT DOCUMENTS

| | | | |
|---|---|---|---|
| 4,582,905 A | | 4/1986 | Sakai |
| 5,958,965 A | | 9/1999 | Mewshaw et al. |
| 6,187,805 B1 | | 2/2001 | Pineiro et al. |
| 6,509,357 B1 | * | 1/2003 | Zhou et al. ............ 514/322 |

FOREIGN PATENT DOCUMENTS

| | | |
|---|---|---|
| JP | 4134064 A2 | 5/1992 |
| WO | WO 95/17398 A | 6/1995 |
| WO | WO 97/25041 A1 | 7/1997 |
| WO | WO 02/32863 A1 | 4/2002 |
| WO | WO 02/36562 A2 | 5/2002 |
| WO | WO 02/41889 A2 | 5/2002 |
| WO | WO 02/059088 A1 | 8/2002 |
| WO | WO 02/085853 A2 | 10/2002 |
| WO | WO 02/085892 A1 | 10/2002 |

OTHER PUBLICATIONS

Sakai, Makiko, "Selective Cleavage of Unsymmetrical 2,2–spiro–1,3–dioxolanes. II. Cleavage of ketal ring of 5'–bromo–6', 7'–dihydro–4–isopropylaminomethyl–1'–p–toluenesulfonylspiro[1,3–dioxolane–2,4'–(5'H)–indole] and its analogs," *Heterocycles*, (1982), pp. 1269–1275, 19(7).

Fuji, Masahiro, et al., "Preparation of Alkyl–Substituted Indoles in the Benzene Portion. Part 7. Synthesis of (+ or –) and (S) —(–)–pindolol," *Chemical Pharm. Bulletin*, (1992), pp. 2353–2357, 40(9).

* cited by examiner

Primary Examiner—Charanjit S. Aulakh
(74) Attorney, Agent, or Firm—Robert C. Hall

(57) ABSTRACT

The present invention provides a compound of the formula:

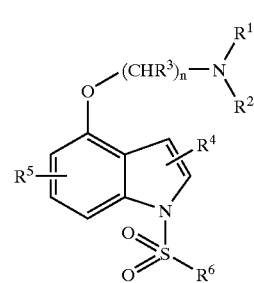

a pharmaceutically acceptable salt or a prodrug thereof, where $R^1$, $R^2$, $R^3$, $R^4$, $R^5$, $R^6$, and n are as defined herein. The present invention also provides compositions comprising, methods for using, and methods for preparing Compound of Formula I.

1 Claim, No Drawings

1-SULFONYL-4-AMINOALKOXY INDOLE DERIVATIVES AND USES THEREOF

CROSS-REFERENCE TO RELATED APPLICATIONS

This application claims the benefit under Title 35 U.S.C. 119(e) of U.S. Provisional Application No. 60/386,049, filed Jun. 5, 2002.

FIELD OF THE INVENTION

This invention relates to 1-sulfonyl-4-aminoalkoxy indole derivatives, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8. 5-HT6 antagonists have also been identified as potentially useful compounds for treatment of obesity. See for example, Bentley et al., *Br. J. Pharmac.* 1999, Suppl 126; Bently et al., *J. Psychopharmacol.* 1997, Suppl A64: 255; Wooley et al., *Neuropharmacology* 2001, 41: 210–129; and WO 02/098878.

While some 5-HT6 modulators have been disclosed, there continues to be a need for compounds that are useful for modulating 5-HT6.

SUMMARY OF THE INVENTION

The present invention provides a compound of the formula:

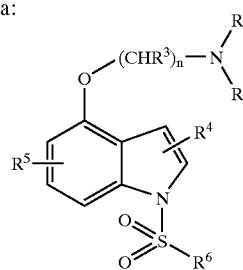

I a pharmaceutically acceptable salt or a prodrug thereof, wherein n is 2 or 3;

each of $R^1$ and $R^2$ is independently hydrogen, lower alkyl, or $R^1$ and $R^2$ together with the nitrogen atom to which they are attached may form a heterocyclyl group;

each $R^3$ is independently hydrogen or alkyl, or $R^3$ and $R^1$ together with the nitrogen atom to which $R^1$ is attached may form a four to seven membered ring moiety with $R^1$ and $R^3$ together forming an alkylene group;

$R^4$ is hydrogen, lower alkyl, or haloalkyl;

$R^5$ is hydrogen, lower alkyl, halo, alkoxy, or haloalkyl; and $R^6$ is optionally substituted aryl or optionally substituted heteroaryl.

The present invention also provides methods for preparing, compositions comprising, and methods for using Compounds of Formula I.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, preferably one to four carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —$OR^z$, wherein $R^z$ is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono- or bicyclic aromatic ring. The aryl group can optionally be substituted with one, two or three, preferably one or two, substituents, wherein each substituent is independently lower alkyl, halo, alkoxy, sulfonyl, cyano, cycloalkyl, heterocyclyl, unless otherwise specifically indicated. In addition, a substituted aryl also includes a cycloalkyl and/or a heterocyclyl group that is fused to the aryl moiety. Examples of aryl moieties include, but are not limited to, optionally substituted phenyl and optionally substituted naphthyl, and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated.

Examples of cycloalkyl moieties include, but are not limited to, cyclopropyl, cyclobutyl, cyclopentyl, cyclohexyl, cycloheptyl, and the like.

"Disease state" means any disease, condition, symptom, or indication.

The terms "halo" and "halogen" are used interchangeably herein and refer to a substituent fluoro, chloro, bromo, or iodo, preferably fluoro or chloro.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. Heteroaryl can optionally be substituted with one, two, or three, preferably, one or two, substituents, wherein each substituent is independently lower alkyl, halo, alkoxy, sulfonyl, cyano, cycloalkyl, heterocyclyl, unless otherwise specifically indicated. In addition, a substituted heteroaryl also includes a cycloalkyl and/or a heterocyclyl group that is fused to the heteroaryl moiety. Examples of heteroaryl moieties include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, isoindolyl, and the like.

"Heterocyclyl" means a monovalent saturated moiety, consisting of one to three rings, incorporating one, two, or three heteroatoms (chosen from nitrogen, oxygen or sulfur). Examples of heterocyclyl moieties include, but are not limited to, morpholino, piperazinyl, piperidinyl, pyrrolidinyl, tetrahydropyranyl, azetidinyl, and the like.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Similarly, the term "hydroxy protecting group" refers to those organic groups intended to protect the oxygen atom of a hydroxyl group against undesirable reactions during synthetic procedures. Exemplary hydroxy protecting groups include, but are not limited to benzyl, silyl groups, tetrahydropyranyl, esters, and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® v. 2.2. Any open valency on a carbon, nitrogen or oxygen atom in the chemical structures herein should be understood as indicating the presence of a hydrogen.

Compounds of the Invention

In one aspect, the present invention provides a compound of the formula:

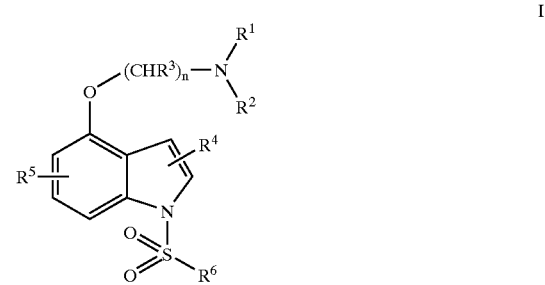

I a pharmaceutically acceptable salt or a prodrug thereof, wherein n is 2 or 3; preferably n is 2;

each of $R^1$ and $R^2$ is independently hydrogen, lower alkyl, or $R^1$ and $R^2$ together with the nitrogen atom to which they are attached may form a heterocyclyl group;

each $R^3$ is independently hydrogen or alkyl, or $R^3$ and $R^1$ together with the nitrogen atom to which $R^1$ is attached may form a four to seven membered ring moiety with $R^1$ and $R^3$ together forming an alkylene group;

$R^4$ is hydrogen, lower alkyl, or haloalkyl; preferably $R^4$ is hydrogen;

$R^5$ is hydrogen, lower alkyl, halo, alkoxy, or haloalkyl; preferably $R^5$ is hydrogen; and $R^6$ is optionally substituted aryl or optionally substituted heteroaryl.

It is to be understood that the scope of this invention encompasses not only the various isomers which may exist but also the various mixture of isomers which may be formed. Furthermore, the scope of the present invention also encompasses solvates and salts of Compounds of Formula I.

In one embodiment, $R^6$ is optionally substituted aryl. Preferably, $R^6$ is phenyl, 3-chlorophenyl, 2-fluorophenyl, naphth-1-yl, 4-fluorophenyl, 3-trifluoromethylphenyl, 3-fluorophenyl, 2,4-difluorophenyl, 2-cyanophenyl, 4-methoxyphenyl, 3-chloro-4-fluorophenyl, 5-fluoro-2-methylphenyl, 2-methanesulfonylphenyl, 2-methylphenyl, N-acetyl 4-aminophenyl, or 4-acetylphenyl. More preferably $R^6$ is phenyl or 2-fluorophenyl.

In another embodiment, $R^6$ is optionally substituted heteroaryl. Preferably, $R^6$ is optionally substituted thienyl, pyridinyl, quinolinyl, benzofuryl, or benzothienyl. More preferably, $R^6$ is thien-2-yl, quinolin-8-yl, 5-chlorothien-2-yl.

Still in another embodiment, $R^3$ is hydrogen.

Yet in another embodiment, $R^1$ and $R^3$ together with the nitrogen atom to which $R^1$ is attached to form a four to seven membered ring moiety with $R^1$ and $R^3$ together forming an alkylene group. Preferably, $R^1$ and $R^3$ together with the nitrogen atom to which $R^1$ is attached to form a four-, five-, or six-membered ring moiety. More preferably, $R^1$ and $R^3$ together with the nitrogen atom to which $R^1$ is attached to form a five-membered ring moiety. Still more preferably, $R^1$ and $R^3$ together with the nitrogen atom to which $R^1$ is attached to form pyrrolidin-2-yl or pyrrolidin-3-yl.

In another embodiment, each of $R^1$ and $R^2$ is independently hydrogen or alkyl. Preferably, each of $R^1$ and $R^2$ is independently hydrogen or methyl.

Still yet in another embodiment, $R^1$ and $R^2$ together with the nitrogen atom to which they are attached to form heterocyclyl. Preferably, $R^1$ and $R^2$ together with the nitrogen atom to which they are attached to form azetidinyl, pyrrolidinyl, piperidinyl, piperazinyl, or morpholino. More preferably, $R^1$ and $R^2$ together with the nitrogen atom to which they are attached to form azetidin-3-yl, pyrrolidinyl, or morpholino.

Still further, combinations of the preferred groups described herein will form other preferred embodiments. For example, in one particularly preferred embodiment $R^1$, $R^3$, $R^4$, and $R^5$ are hydrogen, n is 2, $R^6$ is phenyl or 2-fluorophenyl, and $R^2$ is methyl. In this manner, a variety of preferred compounds are embodied within the present invention.

Representative compounds of Formula I in accordance with the invention are shown in Table 1 below as hydrochloride or trifluoroacetic acid salts.

TABLE 1

| Cpd | Ex | Structure | Name (AUTONOM) |
|---|---|---|---|
| 1 | 2 | 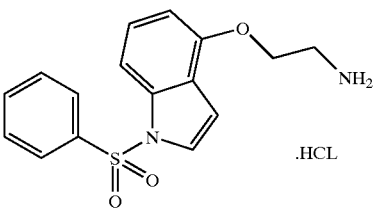 | 2-(1-Benzenesulfonyl-1H-indol-4-yloxy)-ethylamine hydrochloride |
| 2 | 2 | 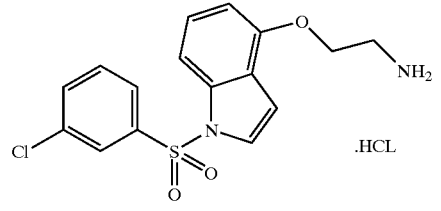 | 2-(1-(3-Chloro-benzenesulfonyl-1H-indol-4-yloxy)-ethylamine hydrochloride |
| 3 | 2 | 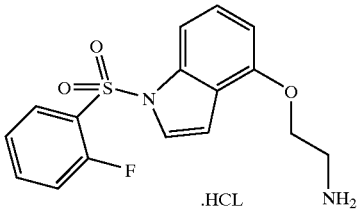 | 2-(1-(2-Fluoro-benzenesulfonyl-1H-indol-4-yloxy)-ethylamine hydrochloride |
| 4 | 1 | 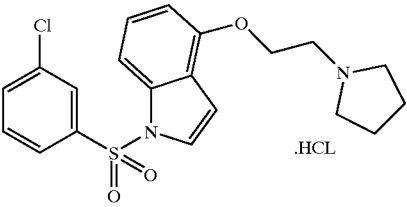 | 1-(3-Chloro-benzenesulfonyl)-4-(2-pyrrolidin-1-yl-ethoxy)-1H-indole hydrochloride |
| 5 | 1 | 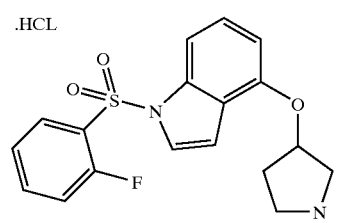 | 1-(2-Fluoro-benzenesulfonyl)-4-(pyrrolidin-3-yloxy)-1H-indole hydrochloride |

TABLE 1-continued

| Cpd | Ex | Structure | Name (AUTONOM) |
|---|---|---|---|
| 6 | 1 | 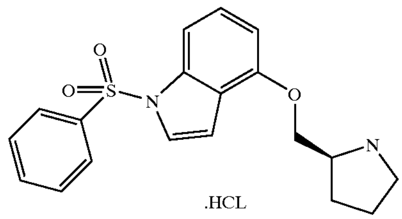 | (S)-1-Benzenesulfonyl-4-(pyrrolidin-2-ylmethoxy)-1H-indole hydrochloride |
| 7 | 2 | 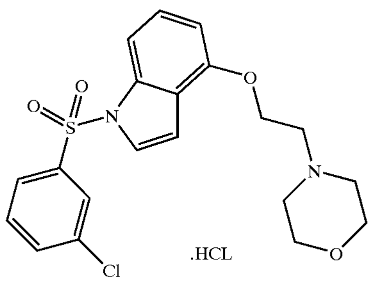 | 1-(3-Chloro-benzenesulfonyl)-4-(2-morpholin-4-yl-ethoxy)-1H-indole hydrochloride |
| 8 | 4 | 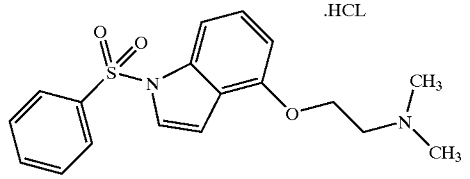 | [2-(1-Benzenesulfonyl-1H-indol-4-yloxy)-ethyl]-dimethyl-amine hydrochloride |
| 9 | 4 | 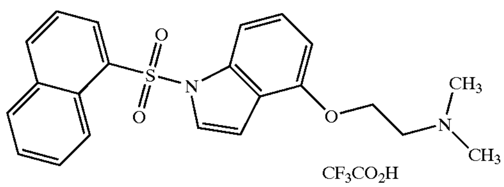 | Dimethyl-{2-[1-(naphthalene-1-sulfonyl)-1H-indol-4-yloxy]-ethyl}-amine trifluoroacetic acid |
| 10 | 4 | 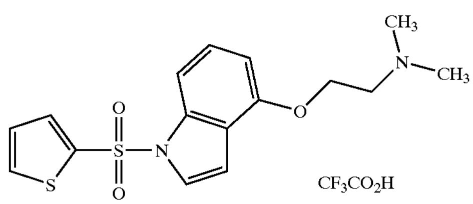 | Dimethyl-{2-[1-(thiophene-2-sulfonyl)-1H-indol-4-yloxy]-ethyl}-amine trifluoroacetic acid |
| 11 | 4 | 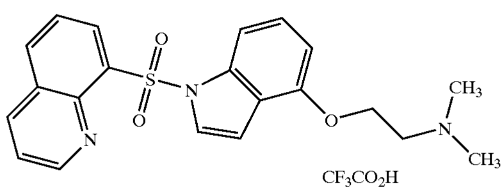 | Dimethyl-{2-[1-(quinoline-8-sulfonyl)-1H-indol-4-yloxy]-ethyl}-amine trifluoroacetic acid |
| 12 | 4 | 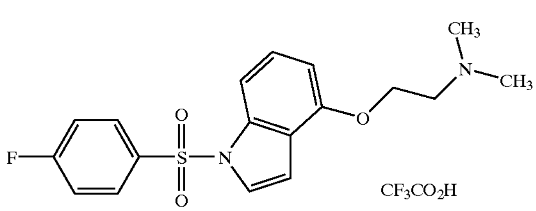 | {2-[1-(4-Fluoro-benzenesulfonyl)-1H-indol-4-yloxy]-ethyl}-dimethyl-amine trifluoroacetic acid |

TABLE 1-continued

| Cpd | Ex | Structure | Name (AUTONOM) |
|---|---|---|---|
| 13 | 4 | 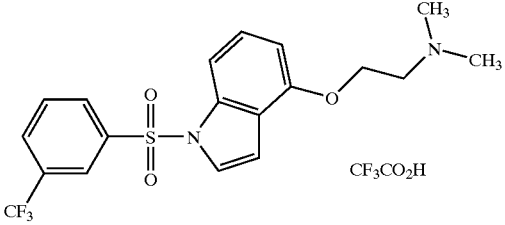 | Dimethyl-{2-[1-(3-trifluoromethyl-benzenesulfonyl)-1H-indol-4-yloxy]-ethyl}-amine trifluoroacetic acid |
| 14 | 4 | 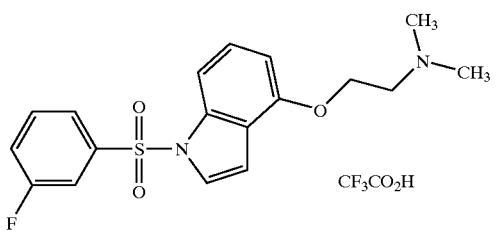 | {2-[1-(3-Fluoro-benzenesulfonyl)-1H-indol-4-yloxy]-ethyl}-dimethyl-amine trifluoroacetic acid |
| 15 | 4 | 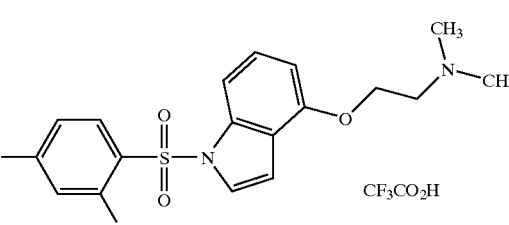 | {2-[1-(2,4-Difluoro-benzenesulfonyl)-1H-indol-4-yloxy]-ethyl}-dimethyl-amine trifluoroacetic acid |
| 16 | 4 | 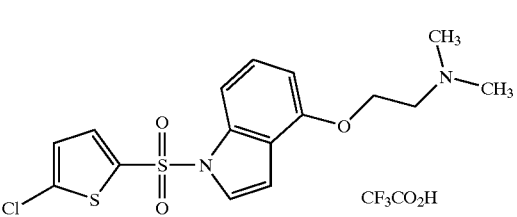 | {2-[1-(5-Chloro-thiophene-2-sulfonyl)-1H-indol-4-yloxy]-ethyl}-dimethyl-amine trifluoroacetic acid |
| 17 | 4 | 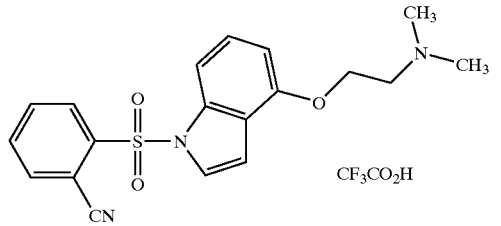 | 2-[4-(2-Dimethylamino-ethoxy)-indole-1-sulfonyl]-benzonitrile trifluoroacetic acid |
| 18 | 4 | 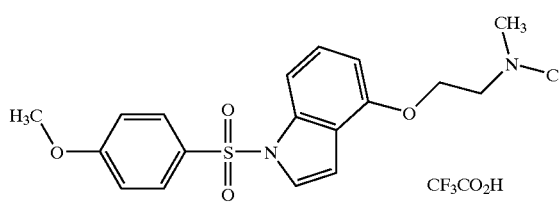 | {2-[1-(4-Methoxy-benzenesulfonyl)-1H-indol-4-yloxy]-ethyl}-dimethyl-amine trifluoroacetic acid |

TABLE 1-continued

| Cpd | Ex | Structure | Name (AUTONOM) |
|---|---|---|---|
| 19 | 4 | 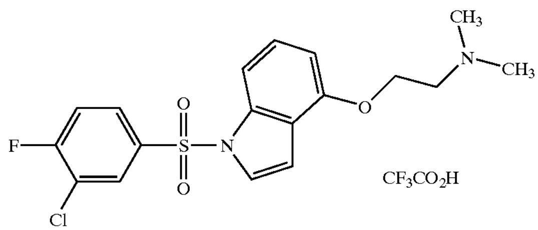 | {2-[1-(3-Chloro-4-fluoro-benzenesulfonyl)-1H-indol-4-yloxy]-ethyl}-dimethyl-amine trifluoroacetic acid |
| 20 | 4 | 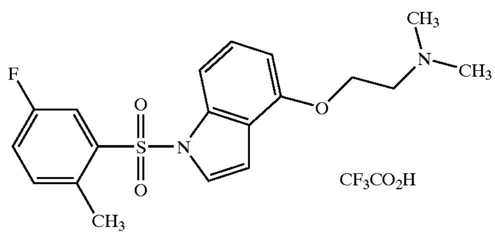 | {2-[1-(5-Fluoro-2-methyl-benzenesulfonyl)-1H-indol-4-yloxy]-ethyl}-dimethyl-amine trifluoroacetic acid |
| 21 | 1 | 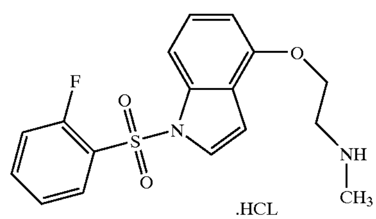 | {2-[1-(2-Fluoro-benzenesulfonyl)-1H-indol-4-yloxy]-ethyl}-methyl-amine hydrochloride |
| 22 | 1 | 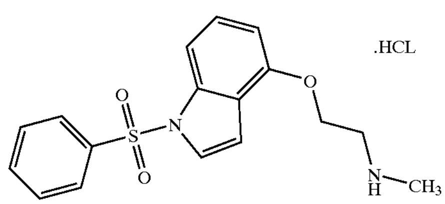 | [2-(1-Benzenesulfonyl-1H-indol-4-yloxy)-ethyl]-methyl-amine hydrochloride |
| 23 | 3 | 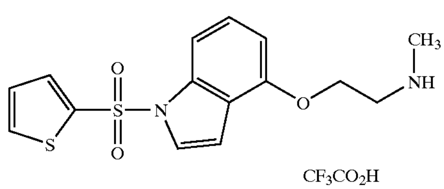 | Methyl-{2-[1-(thiophene-2-sulfonyl)-1H-indol-4-yloxy]-ethyl}-amine trifluoroacetic acid |
| 24 | 3 | 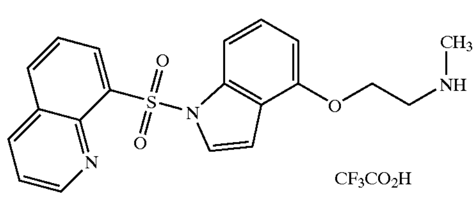 | Methyl-{2-[1-(quinoline-8-sulfonyl)-1H-indol-4-yloxy]-ethyl}-amine trifluoroacetic acid |
| 25 | 3 | 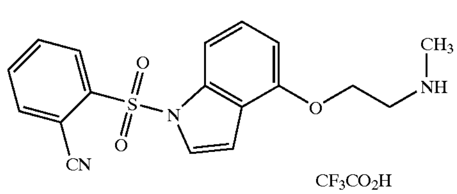 | 2-[4-(2-Methylamino-ethoxy)-indole-1-sulfonyl]-benzonitrile trifluoroacetic acid |

TABLE 1-continued

| Cpd | Ex | Structure | Name (AUTONOM) |
|---|---|---|---|
| 26 | 3 | 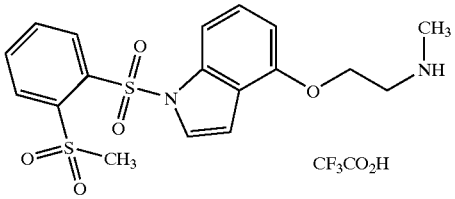 | {2-[1-(2-Methanesulfonyl-benzenesulfonyl)-1H-indol-4-yloxy]-ethyl}-methyl-amine trifluoroacetic acid |
| 27 | 3 | 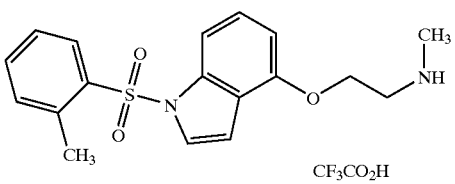 | Methyl-{2-[1-(toluene-2-sulfonyl)-1H-indol-4-yloxy]-ethyl}-amine trifluoroacetic acid |
| 28 | 3 | 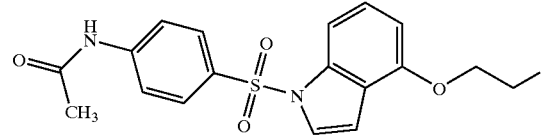 | N-{4-[4-(2-Methylamino-ethoxy)-indole-1-sulfonyl]-phenyl}-acetamide trifluoroacetic acid |
| 29 | 3 | 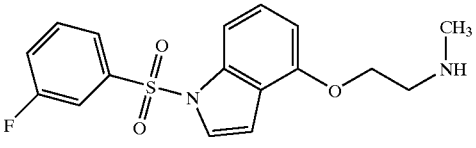 | {2-[1-(3-Fluoro-benzenesulfonyl)-1H-indol-4-yloxy]-ethyl}-methyl-amine trifluoroacetic acid |
| 30 | 3 | 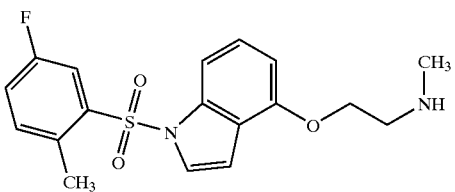 | {2-[1-(5-Fluoro-2-methyl-benzenesulfonyl)-1H-indol-4-yloxy]-ethyl}-methyl-amine trifluoroacetic acid |
| 31 | 3 | 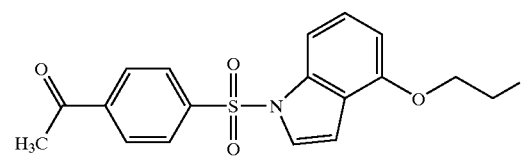 | 1-{4-[4-(2-Methylamino-ethoxy)-indole-1-sulfonyl]-phenyl}-ethanone trifluoroacetic acid |
| 32 | 4 | 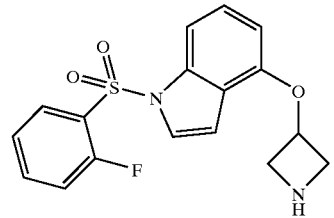 | 4-(Azetidin-3-yloxy)-1-(2-fluoro-benzenesulfonyl)-1H-indole hydrochloride |

TABLE 1-continued

| Cpd | Ex | Structure | Name (AUTONOM) |
|---|---|---|---|
| 33 | 2 | 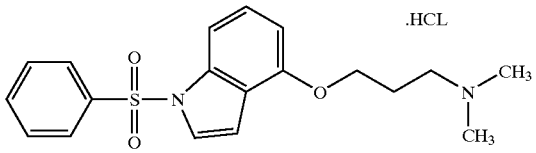 | [3-(1-Benzenesulfonyl-1H-indol-4-yloxy)-propyl]-dimethyl-amine hydrochloride |
| 34 | 1 | 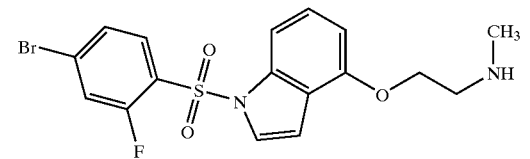 | {2-[1-(4-Bromo-2-fluoro-benzenesulfonyl)-1H-indol-4-yloxy]-ethyl}-methyl-amine hydrochloride |

Another aspect of the present invention provides a composition comprising a therapeutically effective amount of a Compound of Formula I and a pharmaceutically acceptable carrier.

Yet another aspect of the present invention provides a method for treating a CNS disease state in a subject comprising administering to the subject a therapeutically effective amount of a Compound of Formula I. Preferably, the disease state comprises psychoses, schizophrenia, manic depressions, neurological disorders, memory disorders, attention deficit disorder, Parkinson's disease, amyotrophic lateral sclerosis, Alzheimer's disease and Huntington's disease.

Still another aspect of the present invention provides a method for treating a disorder of the gastrointestinal tract in a subject comprising administering to the subject a therapeutically effective amount of a Compound of Formula I.

Another aspect of the present invention provides a method for producing a Compound of Formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,* Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In one embodiment, Compounds of Formula I, are prepared by alkylating a 4-hydroxyl-1-sulfonyl indole compound of the formula:

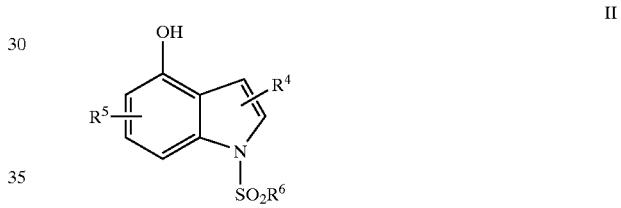

II with an alkylating compound of the formula:

III to produce the compound of Formula I, where $R^1$, $R^2$, $R^3$, $R^4$, $R^5$, $R^6$, and n are those defined herein; and Y is a leaving group. Suitable leaving groups include halides, such as chloride, bromide, and iodine. Alternatively, the leaving group can be formed in situ, for example, by reacting a hydroxide group with a mixture of triphenyl phosphine and diethylazodicarboxylate (DEAD), and the like.

The alkylation reaction between Compound of Formulas II and III is typically conducted by using a leaving group that is formed by in situ from a reaction between the hydroxide group of the Compound of Formula III (i.e., Y is —OH) with a mixture of triphenyl phosphine and DEAD in an inert organic solvent, such as tetrahydrofuran (i.e., THF).

The alkylation reaction of a Compound of Formula II with a Compound of Formula III is generally conducted at below room temperature, typically at about 0° C. However, it should be appreciated that the alkylation reaction temperature is not limited to this particular temperature. The alkylation reaction temperature can vary significantly depending on the nature of the substrate as well as other factors, such as the leaving group, the solvent used, and, the concentrations of each components, etc.

The reaction time for alkylation of a Compound of Formula II with a Compound of Formula III can also vary widely depending on a variety of factors, such as those mentioned above. Generally, the coupling reaction time ranges from about few hours to few days, preferably from about 1 hours to about 100 hours, with about 12 to 72 hours being a typical alkylation reaction time.

Alternatively, the 4-hydroxyl-1-sulfonyl indole compound of Formula II can be alkylated with a cyano compound of the formula: Y—$CH_2$—CN in an inert organic solvent, such as acetonitrile. Preferably, Y is a halide, for example, iodide. Such alkylation reaction is generally conducted in the presence of a base, such as a bicarbonate or a carbonate. The reaction temperature generally ranges from 0° C. to about 50° C., preferably from 0° C. to room temperature.

The cyano group is then reduced using a reducing agent to produce a 4-aminoalkoxy-1-sulfonyl indole compound of the formula:

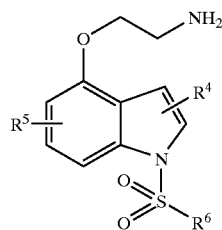

IV

Exemplary reducing agents include hydroboranes, such as borane, cyanoborohydride, and the like. Other suitable reducing agents and reducing conditions are well known to one skilled in the art.

The amino group of Compound of Formula IV can be optionally alkylated with one or more alkylating groups of the formula $R^1$—$X^1$ and $R^2$—$X^2$ to produce the compound of Formula I above, where $R^1$, $R^2$, $R^4$, $R^5$, and $R^6$ are those defined herein; and each of $X^1$ and $X^2$ is independently a leaving group as defined herein.

The 4-hydroxyl-1-sulfonyl indole compound of Formula II can be obtained commercially or can be produced by contacting an indole ether compound of the formula:

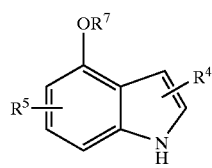

V with a sulfonylating agent of the formula:

VI to produce a 1-sulfonyl indole compound of the formula:

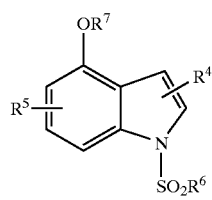

VII and deprotecting the 1-sulfonyl indole compound to produce the 4-hydroxyl-1-sulfonyl indole compound, where $R^4$, $R^5$, and $R^6$ are those defined herein; $R^7$ is a hydroxy protecting group; and X is a sulfonyl activating group. Suitable sulfonyl activating groups are well known to one skilled in the art and include halides, e.g., chloride.

Conditions for removing, i.e., deprotecting, a hydroxy protecting group vary depending on the nature of the protecting group $R^7$. Suitable deprotection reaction conditions are well known to one skilled in the art. See, for example, *Protective Groups in Organic Synthesis*, 3$^{rd}$ edition, T. W. Greene and P. G. M. Wuts, John Wiley & Sons, New York, 1999, which is incorporated herein by reference in its entirety.

Alternatively, Compounds of Formula I can be prepared by reacting a 4-aminoalkoxy indole compound of the formula:

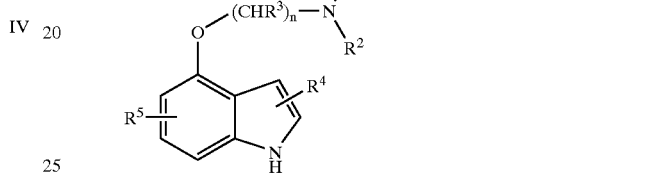

VIII with a sulfonylating agent of the formula:

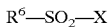

VI where $R^1$, $R^2$, $R^3$, $R^4$, $R^5$, $R^6$, n, and X are those defined herein.

The 4-aminoalkoxy indole compound can be produced by reacting a 4-hydroxy indole compound of the formula:

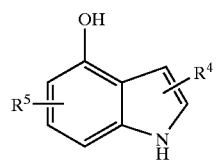

IX with an alkylating compound of the formula:

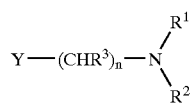

III where $R^1$, $R^2$, $R^3$, $R^4$, $R^5$, n, and Y are those described herein. Suitable alkylation reaction conditions are well known to one skilled in the art and exemplary reaction conditions are described above.

More specific details for producing Compounds of Formula I are described in the Examples section.

Utility

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder.

Testing

The pharmacology of the compounds of this invention was determined by art recognized procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermnal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

This example illustrates a method for producing Compounds of Formula I using the synthetic scheme outlined below:

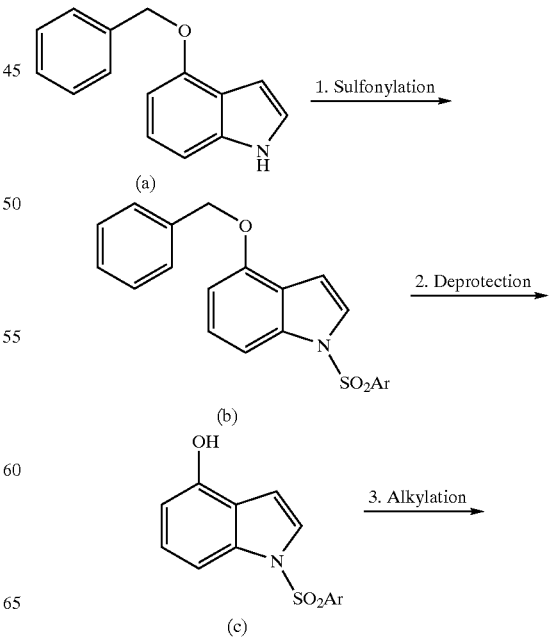

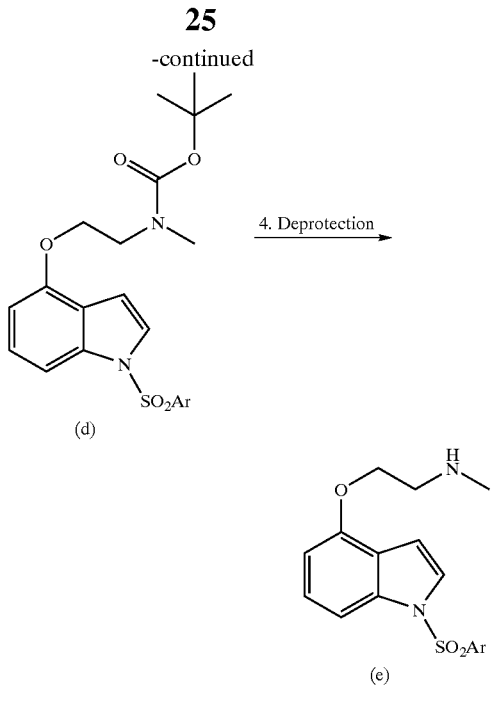

Step 1: Synthesis of 4-benzyloxy-1-(2-fluorobenzene-sulfonyl)-1H-indole

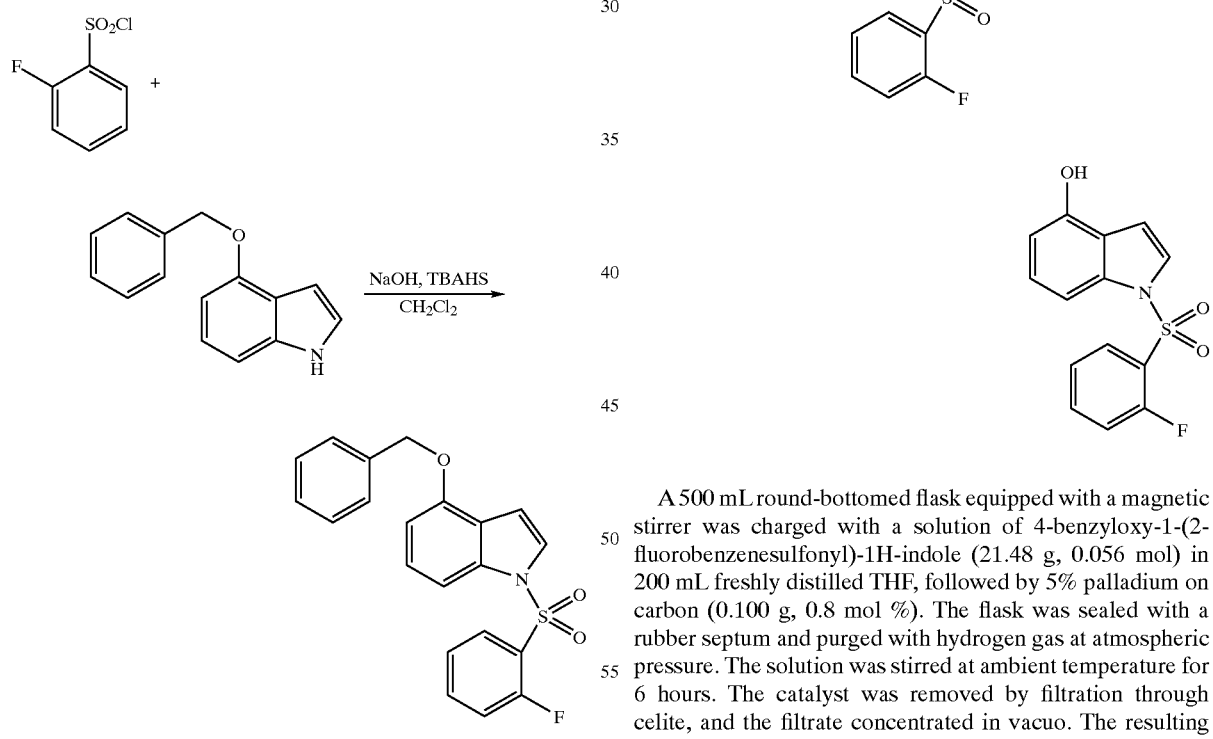

To a magnetically stirred mixture of 4-benzyloxyindole (13.80 g, 0.062 mol), tetrabutylammonium hydrogen sulfate (1.05 g, 0.0031 mol) and finely ground sodium hydroxide (2.72 g, 0.068 mol) in 100 mL of dichloromethane at 0° C., was added 2-fluorobenzenesulfonyl chloride (13.25 g, 0.068 mol). After 18 hours stirring at ambient temperature, 2-fluorobenzenesulfonyl chloride (3.96 g, 0.020 mol) and finely ground sodium hydroxide (0.82 g, 0.020) were added. One hour later, the reaction mixture was washed sequentially with water (2×100 ML) and an aqueous $K_2CO_3$ solution (2 M, 100 mL). The aqueous fractions were combined and extracted with $CH_2Cl_2$ (2×45 mL). The organic fractions were combined, dried over $MgSO_4$ and concentrated in vacuo. The resulting solid was recrystallized from 10:2 ethyl acetate/hexanes (100 mL) to give 4-benzyloxy-1-(2-fluorobenzenesulfonyl)-1H-indole as an off-white powder (21.48 g, 91%). MP 117–120° C.

The following compounds were prepared in a similar fashion using an appropriate sulfonyl chloride.

4-Benzyloxy-1-(3-chlorobenzenesulfonyl)-1H-indole (75%) $^1$H NMR (300 MHz, $CDCl_3$) δ: 5.15 (s, 2 H), 6.73 (d, 1 H, J=8.10), 6.86 (d, 1 H, J=3.77), 7.24 (t, 1 H, J=8.10), 7.26 (m, 1 H), 7.36 (m, 4 H), 7.43 (m, 1 H), 7.44 (m, 1 H), 7.45 (m, 1 H), 7.49 (m, 1 H), 7.59 (d, 1 H, J=8.10), 7.75 (m, 1 H), 7.85 (t, 1 H, J=1.88).

Step 2: Synthesis of 1-(2fluorobenzenesulfonyl)-4-hydroxy-1H-indole

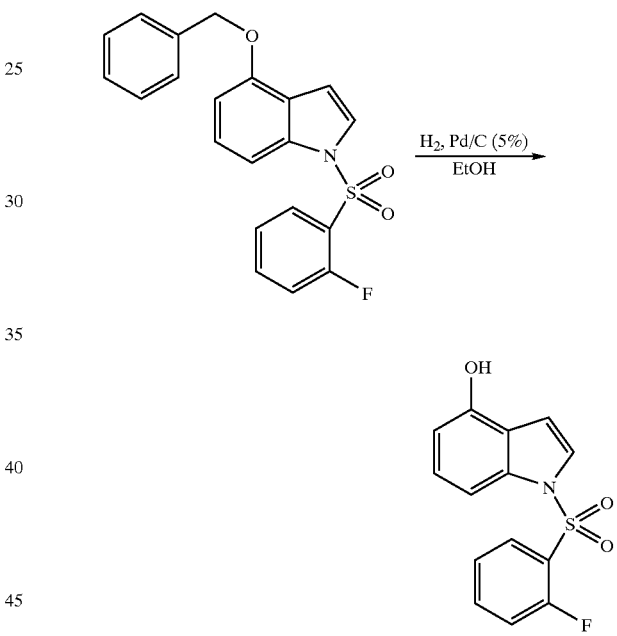

A 500 mL round-bottomed flask equipped with a magnetic stirrer was charged with a solution of 4-benzyloxy-1-(2-fluorobenzenesulfonyl)-1H-indole (21.48 g, 0.056 mol) in 200 mL freshly distilled THF, followed by 5% palladium on carbon (0.100 g, 0.8 mol %). The flask was sealed with a rubber septum and purged with hydrogen gas at atmospheric pressure. The solution was stirred at ambient temperature for 6 hours. The catalyst was removed by filtration through celite, and the filtrate concentrated in vacuo. The resulting crude solid was recrystallized from ethyl ether (75 mL) to give 1-(2-fluorobenzenesulfonyl)-4-hydroxy-1H-indole as a white solid (6.55 g, 40%). MS: (M−H)$^-$=290.1.

The following compounds were prepared in a similar fashion.

1-(3-Chlorobenzenesulfonyl)-4-hydroxy-1H-indole (75%). MS: (M−H)$^-$=306.

1-Benzenesulfonyl-4-hydroxy-1H-indole as a clear oil (48%). MS: (M−H)$^-$=272.2.

Step 3: Synthesis of 2-[1-(2fluorobenzenesulfonyl)-1H-indol-4-yloxy]ethyl methylamine

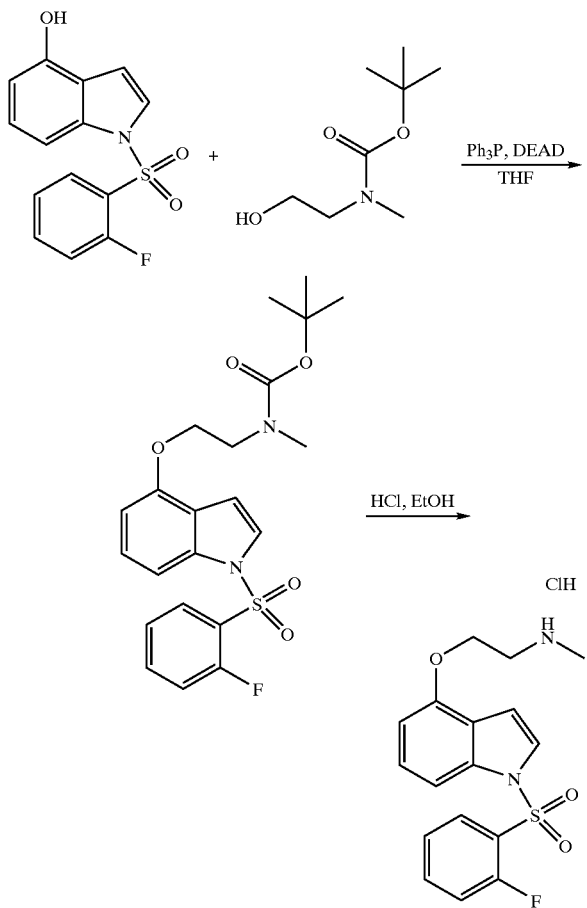

A 100 mL flask equipped with a magnetic stirrer and a rubber septum was charged with triphenyl phosphine (0.506 g, 0.0019 mol) and 1-(2-fluorobenzenesulfonyl)-4-hydroxy-1H-indole (0.330 g, 0.0012 mol), and purged with $N_2$. The mixture was cooled to 0° C. and freshly distilled THF was added (45 mL). A solution of 2-hydroxyethyl methylcarbamic acid tert-butyl ester (0.317 g, 0.0018 mol) and diethylazodicarboxylate (0.337 g, 0.0019 mol) in 5 mL of THF was added dropwise at 0° C. to give a yellow solution. The reaction mixture was warmed to ambient temperature and stirred for 72 hours, concentrated in vacuo and the resulting crude oil was purified by flash chromatography using a 25:75 of hexanes/ethyl acetate mixture to give 2-[1-(2-fluorobenzenesulfonyl)-1H-indol-4-yloxy]ethyl methylcarbamic acid tert-butyl ester as a clear oil (0.483 mg; 89%). $^1$H NMR (300 MHz, CDCl$_3$) δ: 1.44 (bs, 9 H), 3.01 (s, 3 H), 3.65 (bs, 2 H), 4.19 (bs, 2 H), 6.65 (d, 1 H, J=8.03), 6.76 (d, 1 H, J=3.77), 7.09 (t, 1 H, J=8.67). 7.17 (t, 1 H, J=8.11), 7.28 (t, 1 H, J=7.73), 7.44 (d, 1 H, J=8.29), 7.55 (m, 2 H), 803 (t, 1 H, J=7.44).

A solution of 2-[1-(2-fluorobenzenesulfonyl)-1H-indol-4-yloxy]ethyl methylcarbamic acid dimethyl ethyl ester (0.489 g, 0.001 mol) in about 3 mL of EtOH was treated with 1 mL of a solution of 10% hydrogen chloride in ethanol. The solution was heated at 100° C. for 10 minutes, and then cooled to ambient temperature. White precipitate was filtered, washed with about 5 mL of cold ethanol, and dried under vacuum to yield 0.175 g (46%) of 2-[1-(2-fluorobenzenesulfonyl)-1H-indol-4-yloxy]ethyl methylamine. MS: (M+H)$^+$=349, mp 196.9–200.5° C.

Similarly the following compound was prepared:

2-(1-benzenesulfonyl-1H-indol-4-yloxy)ethyl methylamine as a white solid (85%). MS: (M+H)$^+$=331, mp 209.9–212.3° C.

1-Benzenesulfonyl-4-((S)-1-pyrrolidin-2-ylmethoxy)-1H-indole hydrochloride salt. MP=209.2–211.5° C.

1-(2-Fluorobenzenesulfonyl)-4-(pyrrolidin-3-yloxy)-1H-indole hydrochloride salt. MP=106–113.9° C.

1-(3-Chloro-benzenesulfonyl)-4-(2-pyrrolidin-1-yl-ethoxy)-1H-indole hydrochloride salt.

1-(2-Fluoro-benzenesulfonyl)-4-(pyrrolidin-3-yloxy)-1H-indole hydrochloride;

(S)-1-Benzenesulfonyl-4-(pyrrolidin-2-ylmethoxy)-1H-indole hydrochloride salt.

{2-[1-(4-Bromo-2-fluoro-benzenesulfonyl)-1H-indol-4-yloxy]-ethyl}-methyl-amine hydrochloride salt.

For synthesis of 2-hydroxyethyl methylcarbamic acid tert-butyl ester see *J. Med. Chem.* (1999), 42(11), 2007–2020.

Example 2

This example illustrates a method for producing Compounds of Formula I using the synthetic scheme outlined below:

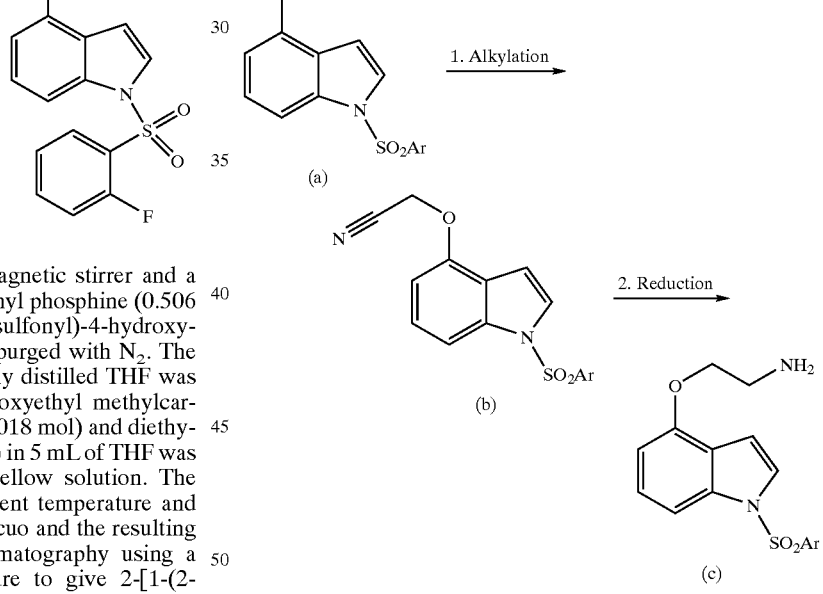

Step 1: Synthesis of [1-(2fluorobenzenesulfonyl)-1H-indol-4-yloxy]acetonitrile

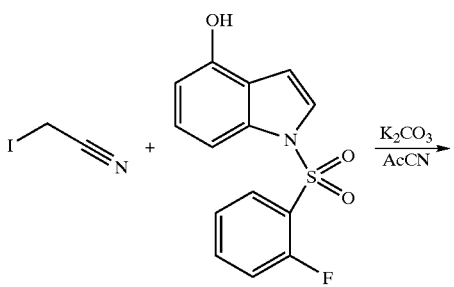

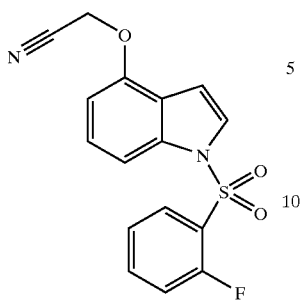

A 50 mL round-bottomed flask equipped with a magnetic stirrer was charged with 1-(2-fluorobenzenesulfonyl)-4-hydroxy-1H-indole (0.600 g, 0.002 mol), 25 mL of anhydrous acetonitrile and potassium carbonate (1.104 g, 0.008 mol). The reaction mixture was cooled to 0° C. and iodoacetonitrile (0.500 g, 0.003 mol) was added dropwise over five minutes. The reaction mixture was allowed to warm to ambient temperature and stirred for eighteen hours. The mixture was taken in ether (200 mL), washed with water (2×30 mL) and brine (1×30 mL), dried over MgSO$_4$ and concentrated in vacuo. The resulting oily brown residue was purified by flash chromatography (8:2 ethyl acetate/hexanes) to give [1-(2-fluoro-benzenesulfonyl)-1H-indol-4-yloxy] acetonitrile as a crystalline solid (0.507 g, 77%). $^1$H NMR (300 MHz, CDCl$_3$) δ: 4.87 (s, 2 H), 6.76 (d, 1 H, J=13.18), 6.77 (d, 1 H, J=1.51), 7.11 (dt, 1 H, J=8.29, J=1.13), 7.23 (t, 1 H, J=8.29), 7.29 (dt, 1 H, J=7.73, J=1.13), 758 (m, 4 H), 8.03 (m, 1 H).

The following compound was prepared in a similar manner.

[1-(3-Chlorobenzenesulfonyl)-1H-indol-4-yloxy] acetonitrile. $^1$H NMR (300 MHz, CDCl$_3$) δ: 4.87 (s, 2 H), 6.77 (d, 1 H, J=8.10), 6.80 (dd, 1 H, J=3.58, J=0.76), 7.30 (t, 1 H, J=8.29), 7.40 (t, 1 H, J=8.10), 7.50 (m, 2 H), 7.73 (m, 2 H), 7.86 (t, 1 H, J=1.88).

Similarly, the following compounds were prepared by reacting a 1-arylsulfonyl-4-hydroxy-1H-indole with an appropriate alkylating agent under alkylation conditions:

3-(1-Benzenesulfonyl-1H-indol-4-yloxy)-propyl-N,N-dimethylamine hydrochloride salt. MS: (M+H)$^+$=359.

1-(3-chlorobenzenesulfonyl)-4-(2-morpholin-4-yl-ethoxy)-1H-indole hydrochloride salt. MP=114.9–115.9° C.

Step 2: Synthesis of 2-(1-(2fluorobenzenesulfonyl-1H-indol-4-yloxy)ethylamine hydrochloride salt

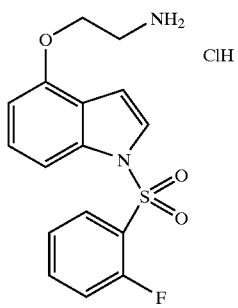

To a solution of [1-(2-fluoro-benzenesulfonyl)-1H-indol-4-yloxy]acetonitrile (0.450 g, 0.0014 mol) in distilled THF (5 mL) at 0° C., borane·THF complex (1M, 2.73 mL, 0.0027 mol) was added dropwise over five minutes with stirring. The reaction mixture was refluxed for three hours and then concentrated in vacuo. The resulting oil was dissolved in 10% ethanolic HCl (10 mL) and refluxed for an additional two hours. The reaction mixture was concentrated in vacuo and the resulting residue was treated with an aqueous sodium hydroxide solution and extracted with ether. The organic layer was dried, filtered, concentrated and purified by flash chromatography (93:7 dichloromethane/methanol) to afford 2-(1(2-fluorobenzenesulfonyl-1H-indol-4-yloxy) ethylamine as a clear oil (0.275 g, 61%). The oil was dissolved in 10% ethanolic HCl (1 mL) and precipitated with about 0.5 mL of ether as 2-(1-(2-fluorobenzenesulfonyl-1 H-indol-4-yloxy)ethylamine hydrochloride salt (0.098 g, 19% over the two steps). MS: (M+H)$^+$=335, mp 147–149.9° C.

The following compounds were prepared in a similar manner.

2-(1-(3-Chlorobenzenesulfonyl-1H-indol-4-yloxy) ethylamine hydrochloride salt. MS: (M+H)$^+$=351.

2-(1-Benzenesulfonyl-1H-indol-4-yloxy)ethylamine hydrochloride salt. MS:(M+H)$^+$=317.

2-(1-Benzenesulfonyl-1H-indol-4-yloxy)-ethylamine hydrochloride salt.

2-(1-(3-Chloro-benzenesulfonyl-1H-indol-4-yloxy)-ethylamine hydrochloride salt.

2-(1-(2-Fluoro-benzenesulfonyl-1H-indol-4-yloxy)-ethylamine hydrochloride salt.

Example 3

This example illustrates a method for producing compounds of Formula I using the synthetic scheme outlined below:

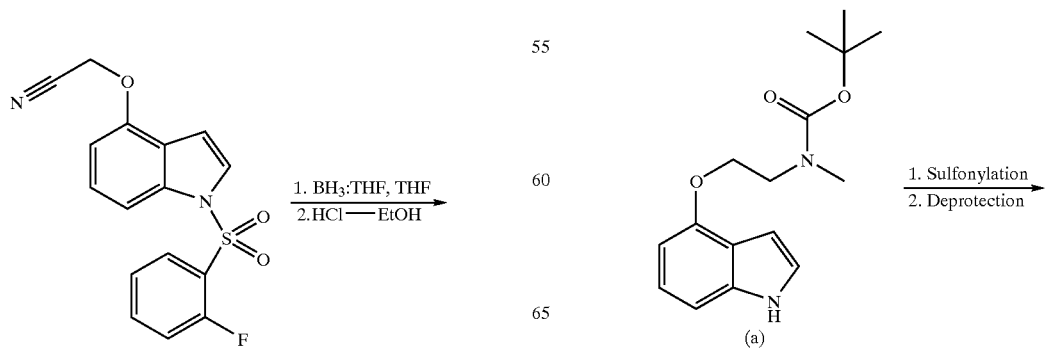

-continued

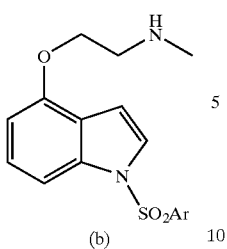

(b)

Step 1: Trifluoroacetic acid salt of methyl 2-[1-(toluene-2-sulfonyl)-1H-indol-4-yloxy]ethylamine

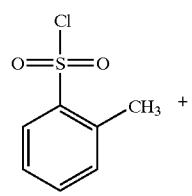

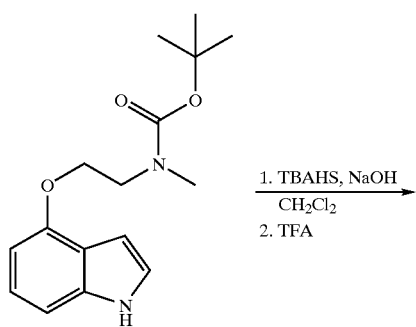

1. TBAHS, NaOH
CH₂Cl₂
2. TFA

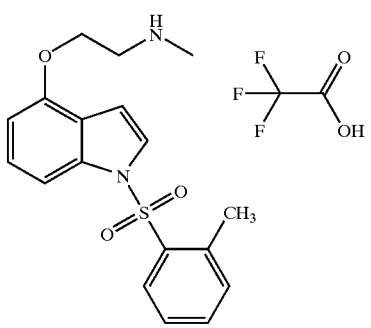

Toluene-2-sulfonyl chloride (0.011 g, 60 μmol) was added to a solution of 2-(1H-indol-4-yloxy)ethyl methylcarbamic acid tert-butyl ester (0.015 g, 50 μmol) and tetrabutylammonium hydrogensulfate (0.00085 g, 2.5 μmol) in 500 μL of CH₂Cl₂ containing 2 N NaOH (100 μL, 200 μmol). After 18 hours stirring at ambient temperature, water (500 μL) was added. The solution was combined with 0.08 g of hydromatrix (marine diatomate) and 0.08 g of trisamine resin, stirred for three hours, and filtered. The filtrate was combined with trifluoroacetic acid (200 μL), stirred for two hours and concentrated in vacuo. The final product was isolated by preparative RPHPLC (YMC Combiprep ODS-A column, 10–90% acetonitrile/water (with 0.1% trifluoroacetic acid) to afford methyl 2-[1-(toluene-2-sulfonyl)-1H-indol-4-yloxy]ethylamine trifluoroacetic acid salt (0.012 g, 44%.). MS: (M+H)⁺=345.2.

The following compounds were prepared in a similar manner using an appropriate arylsulfonyl chloride.

Methyl 2-[1-(thiophene-2-sulfonyl)-1H-indol-4-yloxy]ethylamine trifluoroacetic acid salt. MS: (M+H)⁺=337.1.

Methyl 2-[1-(quinoline-8-sulfonyl)-1H-indol-4-yloxy]ethylamine trifluoroacetic acid salt. MS: (M+H)⁺=382.1.

2-[4-(2-Methylaminoethoxy)-indole-1-sulfonyl]benzonitrile trifluoroacetic acid salt. MS: (M+H)⁺=382.1.

2-[1-(2-Methanesulfonyl-benzenesulfonyl)-1H-indol-4-yloxy]ethyl methylamine trifluoroacetic acid salt. MS: (M+H)⁺=409.2.

N-{4-[4-(2-Methylaminoethoxy)-indole-1-sulfonyl]phenyl}acetamide trifluoroacetic acid salt. MS: (M+H)⁺=388.2.

2-[1-(3-Fluorobenzenesulfonyl)-1H-indol-4-yloxy]ethyl methylamine trifluoroacetic acid salt. MS: (M+H)⁺=349.2.

2-[1-(5-Fluoro-2-methyl-benzenesulfonyl)-1H-indol-4-yloxy]ethyl methylamine trifluoroacetic acid salt. MS: (M+H)⁺=363.2.

1-{4-[4-(2-Methylamino-ethoxy)-indole-1-sulfonyl]phenyl}ethanone trifluoroacetic acid salt. MS: (M+H)⁺=373.1.

For synthesis of 2-(1H-indol-4-yloxy)ethyl methylcarbamic acid tert-butyl ester see *J. Med. Chem.* (1999), 42(11), 2007–2020.

Example 4

This example illustrates a method for producing Compounds of Formula I using the synthetic scheme outlined below:

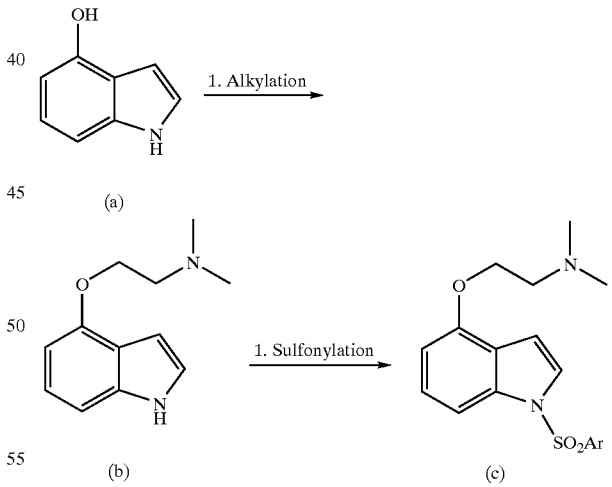

Step 1: Synthesis of 2-(1H-indol-4-yloxy)ethyl dimethylamine

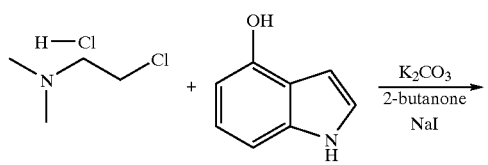

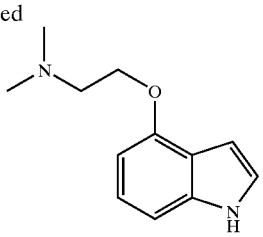

A 100 mL round-bottomed flask equipped with magnetic stirrer and a reflux condenser was charged with 2-butanone (30 mL), 4-hydroxy-1H-indole (1.197 g, 0.009 mol), potassium carbonate (44.71 g, 0.036 mol) and sodium iodide (0.137 g, 0.0009 mol). To this mixture was added 2-chloro-N,N-dimethylethylamine hydrochloride (1.43 g, 0.010 mol). The reaction mixture was brought to reflux and stirred for 24 hours. The solvent was removed in vacuo and the resulting crude residue was dissolved in 60 mL of ethyl acetate and the solution was washed sequentially with water (3×45 mL) and brine (1×45 mL). The aqueous fractions were extracted with ethyl acetate (2×20 mL) and the combined organic fractions were dried over MgSO₄ and concentrated in vacuo. The residue was purified by flash chromatography (95:4.9:0.1 dichloromethane/methanol/ammonium hydroxide) to afford 2-(1H-indol-4-yloxy)ethyl dimethylamine as a transparent pale blue oil (1.322 g, 72%). MS: (M+H)⁺=205.4.

Step 1: Synthesis of 2-(1-benzenesulfonyl-1H-indol-4-yloxy)ethyl dimethylamine hydrochloride salt

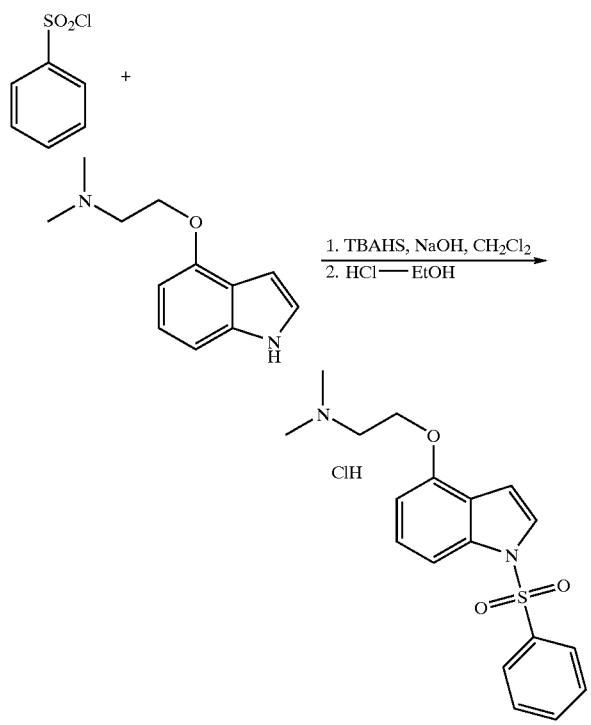

To a mixture of 2-(1H-indol-4-yloxy)ethyl dimethylamine (0.300 g, 0.0015 mol), tetrabutylammonium hydrogen sulfate (0.025 g, 0.000073 mol) and finely ground sodium hydroxide (0.065 g, 0.0016 mol) in 20 mL of CH₂Cl₂ at 0° C. was added benzenesulfonyl chloride (0.286 g, 0.0016 mol). After 18 hours stirring at ambient temperature, the reaction mixture was diluted with 40 mL of CH₂Cl₂ and washed sequentially with water (2×20 mL) and an aqueous K₂CO₃ solution (2 M, 20 mL). The aqueous layers were combined and extracted with CH₂Cl₂ (2×20 mL). The organic fractions were combined, dried over MgSO₄ and concentrated in vacuo. The residue was purified by flash chromatography (10:89.9:0.1 methanol/ethyl acetate/ammonium hydroxide) and the resulting oil was dissolved in boiling 10% ethanolic HCl (3 mL). From this solution, 2-(1-benzenesulfonyl-1H-indol-4-yloxy)ethyl dimethylamine hydrochloride salt was crystallized as a fine pink crystal (0.150 mg, 26%). MS: (M+H)⁺=345, mp 136–140° C.

Synthesis of dimethyl 2-[1-(naphthalene-1-sulfonyl)-1H-indol-4-yloxy]ethylamine trifluoroacetic acid salt

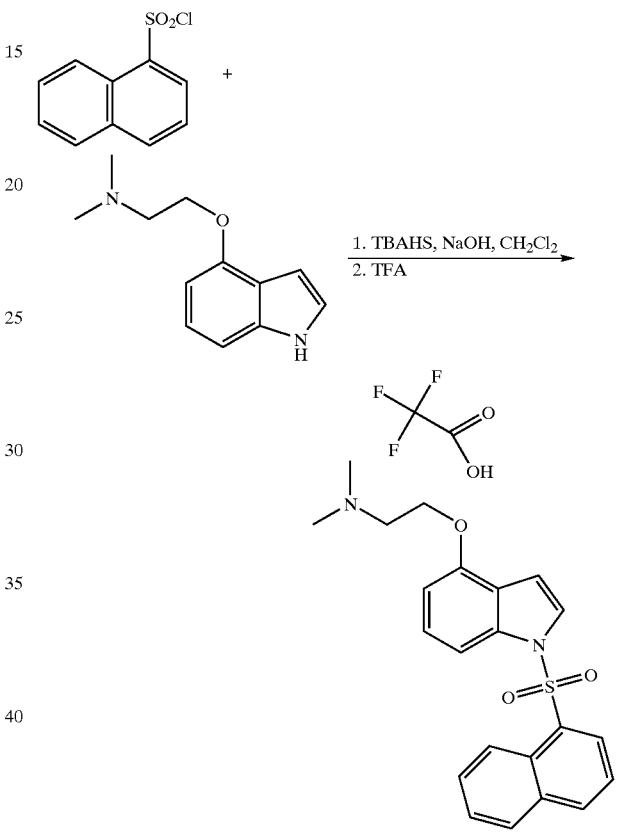

Naphthylene-1-sulfonyl chloride (0.012 g, 60 µmol) was added to a solution of 2-(1H-indol-4-yloxy)ethyl dimethylamine (0.015 g, 50 µmol) and tetrabutylammonium hydrogensulfate (0.00085 g, 2.5 µmol) in 500 µL of CH₂Cl₂. To this solution was added powdered sodium hydroxide (0.007 g, 280 µmol). After 48 hours stirring at ambient temperature, water (500 µL) was added. The solution was filtered through 0.08 g of hydromatrix (marine diatomate) and the hydromatrix was washed with 1 mL of CH₂Cl₂. After concentration of the organic layer in vacuo, the crude residue was purified by preparative RPHPLC (YMC Combiprep ODS-A column, 10–90% acetonitrile/water (with 0.1% trifluoroacetic acid) to afford dimethyl 2-[1-(naphthalene-1-sulfonyl)-1H-indol-4-yloxy]ethylamine trifluoroacetic acid salt (0.006 g, 24%). MS: (M+H)⁺=395.3.

The following compounds were prepared in a similar manner using an appropriate arylsulfonyl chloride.

Dimethyl 2-[1-(thiophene-2-sulfonyl)-1H-indol-4-yloxy]ethylamine trifluoroacetic acid salt. MS: (M+H)⁺=351.2.

Dimethyl 2-[1-(quinoline-8-sulfonyl)-1H-indol-4-yloxy]ethylamine trifluoroacetic acid salt. MS: (M+H)⁺=396.3.

2-[1-(4-Fluorobenzenesulfonyl)-1H-indol-4-yloxy]ethyl dimethylamine trifluoroacetic acid salt. MS: (M+H)+=363.3.

Dimethyl 2-[1-(3-trifluoromethylbenzenesulfonyl)-1H-indol-4-yloxy]ethylamine trifluoroacetic acid salt. MS: (M+H)+=413.

2-[1-(3-Fluorobenzenesulfonyl)-1H-indol-4-yloxy]ethyl dimethylamine trifluoroacetic acid salt. MS: (M+H)+=363.3.

2-[1-(2,4-Difluorobenzenesulfonyl)-1H-indol-4-yloxy]ethyl dimethylamine trifluoroacetic acid salt. MS: (M+H)+=381.3.

2-[1-(5-Chlorothiophene-2-sulfonyl)-1H-indol-4-yloxy]ethyl dimethylamine trifluoroacetic acid salt. MS: (M+H)+=385.2.

2-[4-(2-Dimethylaminoethoxy)indole-1-sulfonyl]benzonitrile trifluoroacetic acid salt. MS: (M+H)+=370.3.

2-[1-(4-Methoxybenzenesulfonyl)-1H-indol-4-yloxy]ethyl dimethylamine trifluoroacetic acid salt. MS: (M+H)+=375.3.

2-[1-(3-Chloro-4-fluorobenzenesulfonyl)-1H-indol-4-yloxy]ethyl dimethylamine trifluoroacetic acid salt. MS: (M+H)+=397.2.

2-[1-(5-Fluoro-2-methylbenzenesulfonyl)-1H-indol-4-yloxy]ethyl dimethylamine trifluoroacetic acid salt. MS: (M+H)+=377.3.

[2-(1-Benzenesulfonyl-1H-indol-4-yloxy)-ethyl]-dimethyl-amine hydrochloride salt.

4-(Azetidin-3-yloxy)-1-(2-fluoro-benzenesulfonyl)-1H-indole hydrochloride salt.

Example 5

This example illustrates in vitro radioligand binding studies of Compound of Formula I.

The binding activity of compounds of this invention in vitro was determined as follows. Duplicate determinations of ligand affinity are made by competing for binding of [³H]LSD in cell membranes derived from HEK293 cells stably expressing recombinant human 5-HT6 receptor. This cell line was prepared by the method described by Monsma et al., *Molecular Pharmacology*, Vol. 43 pp. 320–327 (1993).

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [³H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [³H] LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{Bmax - \text{basal}}{1 + 10^{-Hill(\log[ligand] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of Example 5, compounds of Formula I were tested and found to be selective 5-HT6 antagonists.

Example 6

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

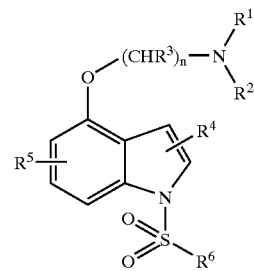

or a pharmaceutically acceptable salt thereof, wherein n is 2 or 3;

each of $R^1$ and $R^2$ is independently hydrogen, lower alkyl, or $R^1$ and $R^2$ together with the nitrogen atom to which they are attached may form a 4 to 6-membered heterocyclyl group;

each $R^3$ is independently hydrogen or alkyl, or one of $R^3$ together with $R^1$ and the atoms there between may form a four to seven membered ring moiety with $R^1$ and $R^3$ together forming an alkylene group;

$R^4$ is hydrogen, lower alkyl, or haloalkyl;

$R^5$ is hydrogen, lower alkyl, halo, alkoxy, or haloalkyl; and $R^6$ is 2-fluorophenyl.

* * * * *